(12) United States Patent
Ancorotti et al.

(10) Patent No.: US 8,895,038 B2
(45) Date of Patent: Nov. 25, 2014

(54) METHOD FOR PREPARING A TWO-COLOURED COSMETIC

(75) Inventors: Renato Ancorotti, Crema (IT); Luigi Gandini, Cavenago di Brianza (IT)

(73) Assignee: Chromavis S.p.A., Milan (IT)

( * ) Notice: Subject to any disclaimer, the term of this patent is extended or adjusted under 35 U.S.C. 154(b) by 2039 days.

(21) Appl. No.: 11/909,689

(22) PCT Filed: Jan. 26, 2006

(86) PCT No.: PCT/IB2006/000121
§ 371 (c)(1),
(2), (4) Date: Oct. 30, 2007

(87) PCT Pub. No.: WO2006/103495
PCT Pub. Date: Oct. 5, 2006

(65) Prior Publication Data
US 2008/0063676 A1    Mar. 13, 2008

(30) Foreign Application Priority Data
Mar. 31, 2005    (IT) .............................. MI2005A0537

(51) Int. Cl.
*A61K 8/02* (2006.01)
*A61Q 1/00* (2006.01)
*A45D 33/00* (2006.01)
*A45D 40/00* (2006.01)
*A61Q 1/02* (2006.01)
*A45D 40/24* (2006.01)

(52) U.S. Cl.
CPC ................ *A61Q 1/02* (2013.01); *A61K 8/0208* (2013.01); *A61Q 1/025* (2013.01); *A45D 40/24* (2013.01); *A45D 33/00* (2013.01)
USPC ......................................................... 424/401

(58) Field of Classification Search
CPC ........................................................ A61Q 1/02
USPC ........................................................... 424/401
See application file for complete search history.

(56) References Cited

U.S. PATENT DOCUMENTS 2,364,388 A * 12/1944 Purinton et al. ............... 264/245

FOREIGN PATENT DOCUMENTS

| JP | 60067408 | 4/1985 |
| JP | 62114907 | 5/1987 |
| JP | 03155803 | 7/1991 |
| WO | 03055453 Y | 7/2003 |
| WO | 2005000256 | 1/2005 |
| WO | 2005084617 | 9/2005 |
| WO | 2005094759 | 10/2005 |

\* cited by examiner

*Primary Examiner* — Rachael E Bredefeld
(74) *Attorney, Agent, or Firm* — Lucas & Mercanti, LLP

(57) ABSTRACT

The invention relates to a method for preparing a two-colour cosmetic product, particularly a two-colour cosmetic product intended for make-up, which consists of a base cosmetic product and a decorative cosmetic product in a different colour being applied onto said base cosmetic product.

6 Claims, 3 Drawing Sheets

METHOD FOR PREPARING A TWO-COLOURED COSMETIC

FIELD OF THE INVENTION

The present invention relates to a method for preparing a two-colour cosmetic product, particularly a two-colour cosmetic product intended for make-up, which consists of a base cosmetic product and a decorative cosmetic product in a different colour being applied onto said base cosmetic product.

BACKGROUND ART

Two-colour cosmetic products are available which are generally prepared by coupling two cosmetic products in different colours in a suitable support base.

Two-colour cosmetic products are also available which are decorated by means of cosmetic products in a different colour on the exposed surface of use.

For example, methods for transferring a decorative product on a base product by means of pads are known, such as described in the Italian Patent Application MI2002A000672 in the name of the same Applicant.

These systems have some limitations of use, and for example they do not allow preparing cosmetic products reproducing particularly complicated shapes or drawings, or still they do not allow using a solid product as the decorative product, for example an extruded product such as described in the International Application WO03/055453 in the name of the same Applicant.

The object of the present invention is to provide a method for preparing two-colour products for make-up.

Another object of the present invention is to provide a method for preparing two-colour products for make-up which are decorated on the surface thereof.

Particularly, an object of the present invention is a method for preparing two-colour products for make-up which consists of a base cosmetic product in a first colour and a decorative cosmetic product in a second colour that is applied on the surface of the base cosmetic product such that both cosmetic products can be seen on the surface exposed to use of the product for make-up and represent a drawing, a figure, a wording, a mark or whatever image.

Another object of the present invention is to provide a method as discussed above, which can be used with cosmetic products for make-up in the form of both compressed powders and solids.

SUMMARY OF THE INVENTION

This and other objects are achieved by means of the method of the present invention for preparing a two-colour cosmetic product for make-up, which comprises:
 a) impressing a desired shape by means of a suitable die on a base cosmetic product in a first colour;
 b) covering said base cosmetic product in a first colour with a decorative cosmetic product in a second colour, and pressing;
 c) removing the excess decorative cosmetic product of a second colour from the surface of the product thus obtained in a sufficient manner as to cause the shape being impressed on the base cosmetic product to rise to the surface.

By the expressions "base cosmetic product in a first colour" and "decorative cosmetic product in a second colour" is meant to designate, according to the present invention, two cosmetic products which are intended for make-up substantially having a similar composition, though in a different colour. These cosmetic products may consist of powders to be pressed or may be compositions obtained by mixing and extruding coloured pastes (also called "slurries"), for example those pastes obtained as described in the International Application WO 03/055453 in the name of the same Applicant. In the latter case, the product for make-up obtained at the end of step (c) will have to be oven-dried for eliminating excess humidity, such as described in the above-mentioned Application.

According to the type of cosmetic product used, the "two-colour cosmetic product for make-up" consists of either pressed powders or pastes that are extruded and then baked, the final product being in this case a solid two-colour cosmetic product for make-up.

By the term "a shape" according to the present invention is meant any drawing, figure, wording, mark, line or image that can be impressed by means of dieing (or coining) on the base cosmetic product.

Accordingly, with the method of the present invention a two-colour product for make-up can be obtained, in which the base cosmetic product in a first colour, which substantially forms the base layer thereof, can be also seen on the surface thereof according to the shape impressed by the die in step (a), whereas the decorative cosmetic product in a second colour covers that portion of base cosmetic product that is excavated by said die.

The annexed figures illustrate a number of the possible embodiments of the invention by way of non-limiting illustration.

DETAILED DESCRIPTION OF A PREFERRED EMBODIMENT OF THE INVENTION

The invention will be now described in detail also with reference to the annexed figures.

In said figures, with 1 is designated the base cosmetic product in a first colour, and with 2 is designated the decorative cosmetic product in a second colour.

In the figures, the two-colour cosmetic product for make-up is shown without any support base or warp, it being understood that a suitable support base is required mainly when the product consists of pressed powders.

Before starting with step (a) of the method of the present invention, a die has to be arranged by suitably shaping a punch which transfers the desired shape by means of pressure.

The die or punch can be of any material suitable for use in the preparation of cosmetic products, such as steel, silicone materials, etc. When powders are used, a layer of powdered base cosmetic product in a first colour has to be arranged in a suitable support base, and stamping is carried out by means of said punch.

When extruded powders are used, said base cosmetic product in a first colour may be either in the form of a "tongue" directly obtained from the extruder, which is either optionally suitably dimensioned, or may be previously subjected to a pre-shaping operation, such as shaped as a half-sphere or truncated pyramid. In this case, the die will also have to be provided with a suitable shape for suitably impressing the desired shape.

Figure 1:
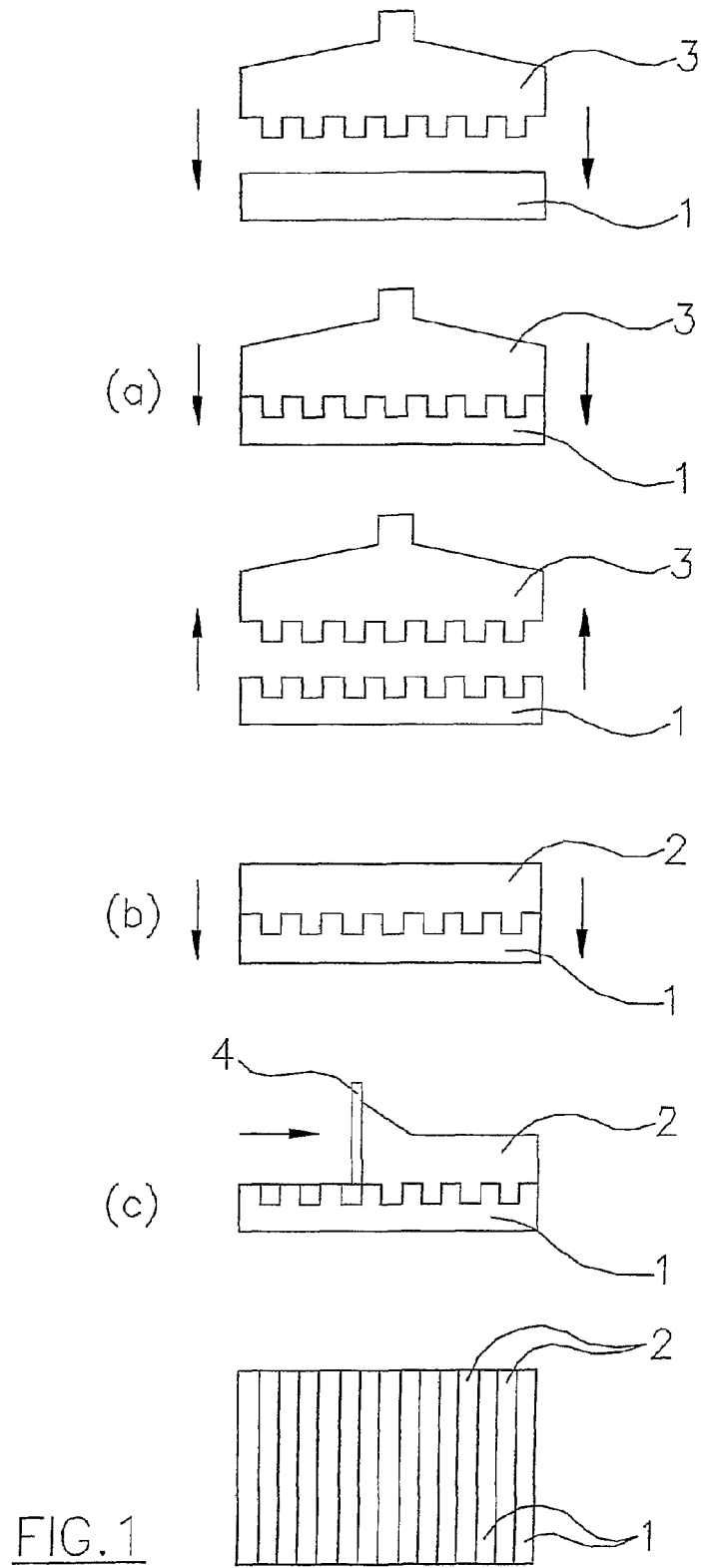
FIG. 1 is a diagram of the method of the present invention.
Figure 2:
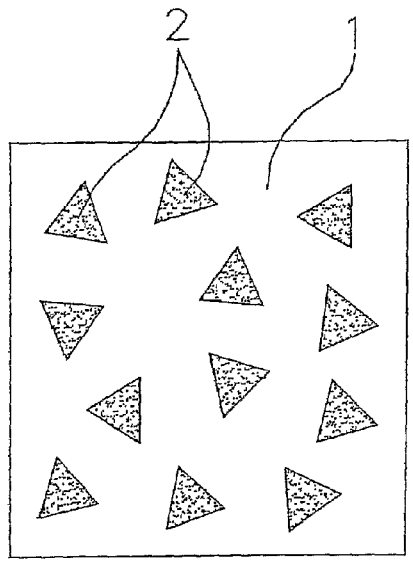
FIGS. 2 and 3 are top views of two embodiments of the invention.
Figure 3:
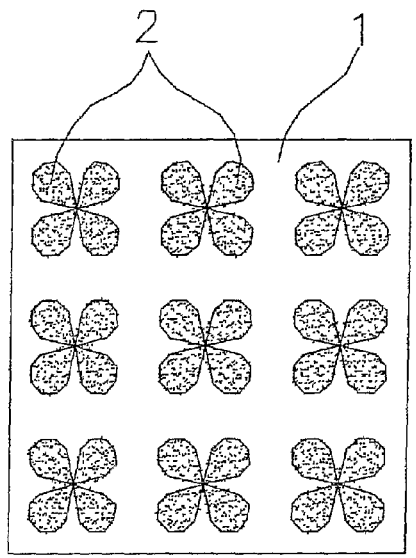
Figure 4:
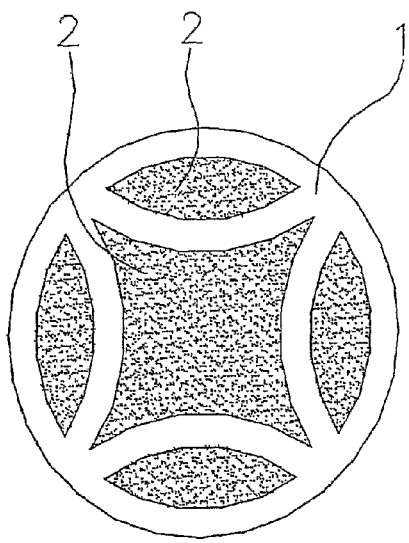
FIGS. 4 and 5 are top and side views of another embodiment of the invention, respectively.
Figure 5:
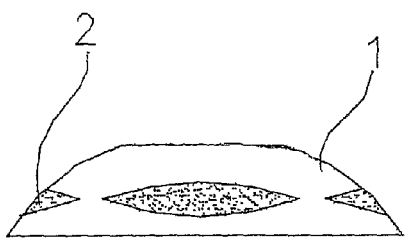

With reference to FIG. 1, in step (a) the die 3 is lowered on the base cosmetic product in a first colour 1, it is pressed in the direction indicated by the arrow and then said die 3 is moved away vertically, the desired shape being thereby obtained.

In step (b) the decorative cosmetic product in a second colour 2 is coated on the base cosmetic product in a first colour 1 and is pressed in the direction indicated by the arrow in FIG. 1.

Alternatively, according to a preferred aspect of the invention, the decorative cosmetic product in a second colour 2 is pressed only on those parts being impressed by the die in step (a), such as by using a die having the same shape as that used in step (a) but with a greater relief (FIG. 6) or yet by using the same die with a different stroke.

Figure 6:
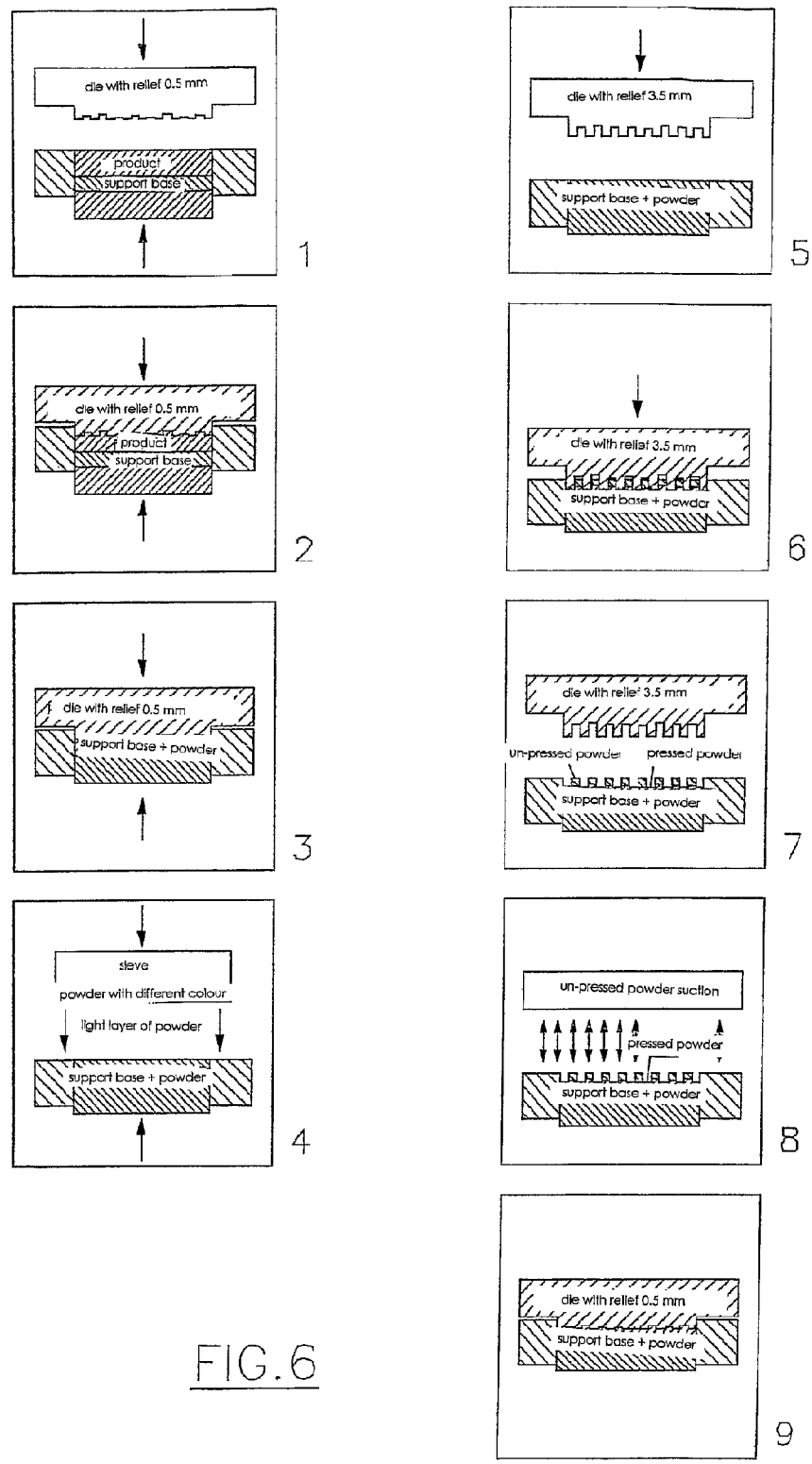
FIG. 6 is a diagram of the method of the present invention according to a particular embodiment.

According to a preferred aspect, with particular reference to FIG. 6, the decorative cosmetic product in a second colour 2 is pressed with the shaped die used in step (a) though having a different relief.

In step (c) the removal of the excess decorative cosmetic product in a second colour from the surface of the product obtained in step (b) is carried out by means of a suitable tool, preferably the removal is provided by a suction device that is suitably calibrated in order to remove only the excess cosmetic product 2 which has not been pressed with the shaped die (FIG. 6); thereby, the shape impressed by the die of the cosmetic product 1 will appear again, the cosmetic product 2 covering the cavities formed in step (a).

Obviously, when extruded pastes are used, the final product has to be subjected to "baking" in an oven at a suitable temperature for allowing the excess humidity to evaporate, such as described in the above-mentioned International Application WO 03/055453.

Accordingly, the invention provides a simple and effective method for obtaining two-colour cosmetic products for make-up that are decorated in a variety of ways on the surface thereof, such as represented in FIG. 2 to 5 in a non-limiting manner.

The result obtained with the method of the present invention is not only restricted to the "decoration" of the surface of a cosmetic product for make-up, but also allows assembling two products for make-up in different colours in an original manner which is particularly appealing to the consumer.

It should be understood, in fact, that according to the characteristics of the die being employed, the amount of cosmetic product 2 that is left at the completion of the step (b) will be more or less considerable, since the latter can either be coated only on the surface of the base cosmetic product 1 or alternatively be a proper component of the two-colour make-up product, particularly when the cavities left by the die allow accommodating considerable amounts of cosmetic product 2 in the final two-colour product.

On the other hand, a surface coating may be used, in addition to the purpose of embellishing the product and making the same more appealing to the consumer of cosmetic products who is normally particularly sensitive to the visual appearance of the product he/she purchases, also to the purpose of applying marks, slogans, images of advertising testimonials, etc., thereby obtaining an effect beyond simple ornament.

The two-colour cosmetic product for make-up obtained with the above-mentioned method is also part of the invention.

The two-colour cosmetic product for make-up obtained with the above-mentioned procedure may be subjected to further processing or treatments such as laser processing, milling, etc.

The final product is then advantageously packaged for trading according to conventional techniques.

The invention claimed is:

1. A method for preparing a two-color cosmetic product for make-up, the method comprising the following steps:
   a) impressing a desired shape by means of a die on a base cosmetic product in a first color having a uniform bottom surface after impressing the desired shape;
   b) covering said base cosmetic product in a first color with a decorative cosmetic product in a second color and pressing; and
   c) removing excess decorative cosmetic product of the second color from a surface of the decorative two-color cosmetic product obtained so as to cause the shape being impressed on the base cosmetic product to rise to the surface;
   wherein said base cosmetic product in the first color and the decorative cosmetic product in the second color are powders to be pressed.

2. The method according to claim 1, characterized in that pressing in step (b) is carried out only on those parts that have been impressed by the die in step (a).

3. The method according to claim 1, characterized in that said base cosmetic product in a first color and decorative cosmetic product in a second color are two cosmetic products intended for make-up having a substantially similar composition though in a different color.

4. The method according to claim 1, wherein in step (a) dieing is carried out on a layer of powdered base cosmetic product in the first color deposited in a support base.

5. The method according to claim 1, wherein said shape is any drawing, figure, wording, mark, line or image.

6. The method according to claim 1, wherein the two-color cosmetic product for make-up obtained, after the two-color cosmetic product has has been optionally subjected to further processing or treatments, is packaged for trading.

* * * * *